(12) United States Patent
Zhang et al.

(10) Patent No.: US 11,022,613 B2
(45) Date of Patent: Jun. 1, 2021

(54) MASS SPECTROMETRY IMAGING OF GLYCANS FROM TISSUE SECTIONS AND IMPROVED ANALYTE DETECTION METHODS

(71) Applicant: THE JOHNS HOPKINS UNIVERSITY, Baltimore, MD (US)

(72) Inventors: Hui Zhang, Ellicott City, MD (US); Xingde Li, Ellicott City, MD (US); Shadi Toghi Eshghi, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 113 days.

(21) Appl. No.: 16/541,581

(22) Filed: Aug. 15, 2019

(65) Prior Publication Data

US 2020/0003783 A1    Jan. 2, 2020

Related U.S. Application Data

(63) Continuation of application No. 15/704,252, filed on Sep. 14, 2017, now Pat. No. 10,436,793, which is a
(Continued)

(51) Int. Cl.
*G01N 33/68* (2006.01)

(52) U.S. Cl.
CPC ..... *G01N 33/6842* (2013.01); *G01N 33/6851* (2013.01); *G01N 2400/12* (2013.01); *G01N 2570/00* (2013.01)

(58) Field of Classification Search
None
See application file for complete search history.

(56) References Cited

U.S. PATENT DOCUMENTS

| | | |
|---|---|---|
| 2005/0118665 A1 | 6/2005 | Zhou et al. |
| 2009/0119027 A1 | 5/2009 | Venkataraman et al. |
| 2014/0329274 A1 | 11/2014 | Bowen et al. |

OTHER PUBLICATIONS

Satomaa, et al., "Analysis of the human cancer glycome identifies a novel group of tumor-associated N-acetylglucosamine glycan antigens", Cancer Research (2009), vol. 69, No. 14, pp. 5811-5819.
(Continued)

*Primary Examiner* — Xiaoyun R Xu
(74) *Attorney, Agent, or Firm* — Casimir Jones, S.C.; Jeffrey W. Childers

(57) ABSTRACT

The presently disclosed subject matter provides methods using mass spectrometry for direct profiling of N-linked glycans from a biological sample. In addition, the embodiments of the present invention also disclose novel methods, known as targeted analyte detection (TAD), for improving the detection limit of MALDI-MS. These methods take advantage of the carrier effect of the added standard analytes, which occurs due to the generic sigmoidal shape of the calibration curve. The functionality of TAD depends on the relative enhancement of sensitivity over the increase of the standard deviation at the analysis of target analytes with spiking in exogenous concentration. At certain ranges of exogenous concentration, the increment in the sensitivity overcomes the standard deviation, resulting in an improved LOD. Theoretically, exogenous concentrations approximately at 1 LODorig would generate the optimum LOD improvement. TAD is a cost-effective LOD improvement method, which is not limited to a certain group of analytes, or detection methods or instruments. It can be applied to enhance the detection of any analyte with different detection methods, provided that the analyte of interest can be extracted or is available in synthetic form.

12 Claims, 19 Drawing Sheets

Related U.S. Application Data continuation of application No. 14/402,478, filed as application No. PCT/US2013/042408 on May 23, 2013, now abandoned.

(60) Provisional application No. 61/650,646, filed on May 23, 2012, provisional application No. 61/681,417, filed on Aug. 9, 2012, provisional application No. 61/776,534, filed on Mar. 11, 2013.

(56) References Cited

OTHER PUBLICATIONS

Duncan, et al., "Quantitative matrix-assisted laser desorption/ionization mass spectrometry", Briefings in Functional Genomics & Proteomics (2008), vol. 7, No. 5, pp. 355-370.
Morelle, et al., "Analysis of protein glycosylation by mass spectrometry", Nature Protocols (2007), vol. 2, No. 7, pp. 1585-1602.
Ruhaak, et al., "N-glycan profiling of dried blood spots", Analytical Chemistry, (Jan. 3, 2012), vol. 84, No. 1, pp. 396-402.
Green, E., et al., "The asparagine-linked oligosaccharides on bovine fetuin" The Journal of Biological Chemistry (1988) vol. 263, No. 34, pp. 18253-18268.
Snovida, S., et al., "Use of a 2,5-dihydroxybenzoic acid/aniline MALDI matrix for improved detection and on-target derivatization of glycans: a preliminary report" Anal. Chem. (2006) vol. 78, No. 24, pp. 8561-8568.
International Search Report and Written Opinion dated Aug. 21, 2013 for PCT application PCT/US2013/042408.
Hortin, et al., Bound Homocysteine, Cysteine, and Cysteinylglycine Distribution between Albumin and Globulins. Clinical chemistry 2006, 52, 1223-37.
Smith. Mass Spectrometry in Biomarker Applications: From Untargeted Discovery to Targeted Verification, and Implications for Platform Convergence and Clinical Application. Clinical chemistry 2012, 58, 528-30.
Krutchinsky, et al., On the mature of the chemical noise in MALDI mass spectra. Journal of the American Society for Mass Spectrometry 2002, 13, 129-34.
Anderson, et al., The human plasma proteome: history, character, and diagnostic prospects. Molecular & Cellular Proteomics 2002, 1, 845-867.
Seeley, et al., Enhancement of Protein Sensitivity for MALDI Imaging Mass Spectrometry After Chemical Treatment of Tissue Sections. Journal of the American Society for Mass Spectrometry 2008, 19, 1069-1077.
Arrigoni, et al., Chemical derivatization of phosphoserine and phosphothreonine containing peptides to increase sensitivity for MALDI-based analysis and for selectivity of MS/MS analysis. Proteomics 2006, 6, 757-766.
Hale, et al., Increased sensitivity of tryptic peptide detection by MALDI-TOF mass spectrometry is achieved by conversion of lysine to homoarginine. Analytical Biochemistry 2000, 287, 110-117.
Sekiya, et al., Derivatization for Stabilizing Sialic Acids in MALDI-MS. Anal Chem 2005, 77, 4962-4968.
Cohen, et al., Influence of Matrix Solution Conditions on the MALDI-MS Analysis of Peptides and Proteins. Analytical Chemistry 1996, 68, 31-37.
Vermillion-Salsbury, et al.,9-Aminoacridine as a matrix for negative mode matrix-assisted laser desorption/ionization. Rapid Communications in Mass Spectrometry 2002, 16, 1575-1581.
Dong, et al., Graphene as a Novel Matrix for the Analysis of Small Molecules by MALDI-TOF MS. Analytical chemistry 2010, 82, 6208-6214.
Towers, et al., Introduction of 4-Chloro-α-cyanocinnamic Acid Liquid Matrices for High Sensitivity UV-MALDI MS. Journal of Proteome Research 2010, 9, 1931-1940.
Xu, et al., Use of Polymer-Modified MALDI-MS Probes to Improve Analyses of Protein Digests and DNA. Analytical chemistry 2004, 76, 3106-11.
Yuan, et al., Protein identification with Teflon as matrix-assisted laser desorption/ionization sample support. Journal of mass spectrometry: JMS 2002, 37, 512-24.
Xu, et al., Patterned Monolayer/Polymer Films for Analysis of Dilute or Salt-Contaminated Protein Samples by MALDI-MS. Analytical chemistry 2003, 75, 185-90.
Schuerenberg, et al., Prestructured MALDI-MS Sample Supports. Analytical chemistry 2000, 72, 3436-42.
Tu, et al., Improving the signal intensity and sensitivity of MALDI mass spectrometry by using nanoliter spots deposited by induction-based fluidics. Journal of the American Society for Mass Spectrometry 2008, 19, 1086-1090.
Nimura, et al., Reduction of the relative error in the standard additions method. Analyst 1990, 115, 1589-1595.
Bellar, et al., Investigation of enhanced ion abundances from a carrier process in high-performance liquid chromatography particle beam mass spectrometry. American Society for Mass Spectrometry 1990, 1, 92-98.
Ediger, et al., The role of chemical modifiers in analyte transport loss interferences with electrothermal vaporization ICP-mass spectrometry. Spectrochimica Acta 1992, 478, 907-922.

- LECTINS
  - CONA: HIGH-MANNOSE GLYCANS
  - SNA: SIALYLATED GLYCANS
  - AAL: FUCOSYLATED GLYCANS

- LIMITATIONS OF LECTIN HISTOCHEMISTRY
  - MINIMAL STRUCTURAL INFORMATION
  - LIMITED TO ONE EPITOPE AT A TIME
  - NOT QUATITATIVE

LECTIN HISTOSTAINING OF
PROSTATE TISSUE WITH AAL
XIANGCHUN WANG, ET AL.
USHUPO ABSTRACT #108.

- SIALIC ACID IS A TERMINAL SUGAR RESIDUE ON N-LINKED GLYCANS
- ANALYSIS OF SIALYLATED N-GLYCANS IS CHALLENGING, BECAUSE SIALIC ACID RESIDUES ARE LOST:
  - BY SAMPLE PREPARATION
  - DURING MASS SPECTROMETRIC ANALYSIS
- LABELING OF SIALIC ACIDS WITH P-TOLUIDINE STABILIZES THESE RESIDUES FOR MS ANALYSIS.

PUNIT SHAH ET AL. ANALYTICAL CHEMISTRY (2013)
TUE AT 10:15 IN CLINICAL GLYCOMICS SESSION

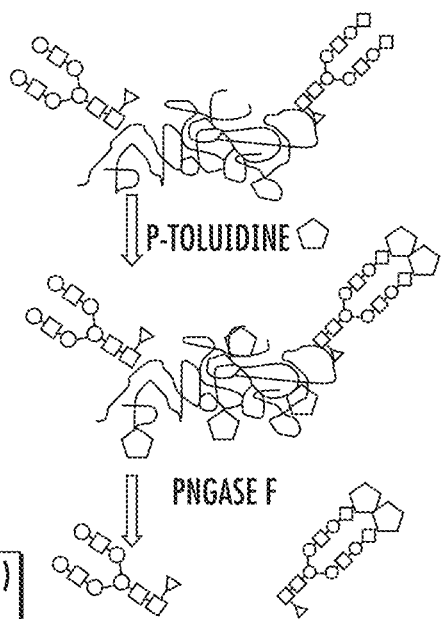

FIG. 7

- MALDI-MS IMAGING TO DIRECTLY PROFILE AND IMAGE LINKED GLYCANS FROM FFPE TISSE SECTIONS
- IN SITU CHEMICAL LABELING OF TISSUE SECTIONS TO IMAGE FFPE TISSUE SECTIONS.
FIG. 10

MASS SPECTROMETRY IMAGING OF GLYCANS FROM TISSUE SECTIONS AND IMPROVED ANALYTE DETECTION METHODS

REFERENCE TO RELATED APPLICATIONS

This application is a Continuation of U.S. patent application Ser. No. 15/704,252, filed Sep. 14, 2017, which is a Continuation of U.S. patent application Ser. No. 14/402,478, filed Nov. 20, 2014, which is a 35 U.S.C. § 371 U.S. national entry of International Application PCT/US2013/042408, having an international filing date of May 23, 2013, which claims the benefit of U.S. Provisional Patent Application Nos. 61/650,646, filed on May 23, 2012, and 61/681,417, filed on Aug. 9, 2012, and 61/776,534, filed Mar. 11, 2013,which are hereby incorporated by reference for all purposes as if fully set forth herein.

FEDERALLY SPONSORED RESEARCH OR DEVELOPMENT

This invention was made with government support under U01CA152813 awarded by the National Institutes of Health (NIH). The government has certain rights in the invention.

BACKGROUND OF THE INVENTION

Glycans play multi-faceted roles in many biological processes and aberrant glycosylation is associated with most of the diseases that affect mankind. Glycans are post-translation modifications of proteins that are involved in cell growth, cytokinesis, differentiation, transcription regulation, signal transduction, ligand-receptor binding, interactions of cells with other cells and extracellular matrix (ECM) and bacterial and viral infection, among other functions (see FIG. 1). Glycan misregulations and structural changes occur in most of the diseases that affect the human.

Lectin histochemistry methods are commonly used to stain tissue glycans on formalin-fixed paraffin-embedded (FFPE) sections (see FIG. 2). Some lectins have high affinities for the epitopes of certain glycans. For example, Concanavalin A (ConA) can be used as a ligand for high-mannose glycans, Sambucus nigra agglutinin (SNA) for sialylated glycans, and Alueria aurantia lectin (AAL) for fucosylated structures. Despite the impact the lectin chemistry has had on the field, it has limitations. For example, lectins provide minimal structural information about the stained epitopes, they are limited to one epitope at a time on each tissue section, they are quantitative and, compared with antibodies, have lower affinities for the glycans. Further, very few monoclonal antibodies have been developed for glycans.

Matrix-assisted laser desorption-ionization time-of-flight mass spectrometry (MALDI-TOF MS) serves as a major technique for fast and accurate analysis of a number of molecules from complex mixtures such as cells, tissues and serum samples. Although MALDI-TOF MS has been successfully applied for detection, identification and validation of many peptides and molecules, it has proven ineffective for analyzing low abundance molecules from complex mixtures. Considering the extremely wide range of protein concentrations in plasma (i.e. from albumin at $10^{10}$ pg/mL to interleukins at 10 pg/mL), the lower-abundant proteins or peptides are dominated by the abundant serum contents and fail to be detected in a mixture. In addition, background and chemical noise (coming from desorbed matrix cluster) interfere with the MS signal and further compromise the sensitivity and detectability for low-abundance analytes. Despite the technological advances in MALDI-TOF instrumentation, the suboptimal transmission efficiency of the mass analyzer, and detection efficiency of the detector, also result in some loss of analyte, which is another factor that reduces the detection limit and sensitivity of MALDI-TOF MS with low-abundant analytes. On the other hand, the concentration of potential disease biomarkers, such as glycans lies in the lower range of concentrations in serum, particularly at the early stages of the disease where screening is crucial.

Therefore, there still exists a need to improve methods for generating structural information of glycans in FFPE sections, as well as the need to improve the sensitivity and detection limits of MALDI-TOF MS analytical methods for glycans, peptides and other target analytes, in order to be effective for biomarker discovery research.

SUMMARY OF THE INVENTION

In accordance with an embodiment, the present invention provides a method for direct profiling of N-linked glycans in a biological sample, the method comprising: (a) obtaining a biological sample comprising at least one glycoprotein; (b) denaturing the at least one glycoprotein in the biological sample; (c) releasing at least one glycan from the at least one glycoprotein; (d) coating the biological sample with a matrix; (e) analyzing the at least one glycan using mass spectrometry; and wherein spatial distribution of the at least one glycan is maintained.

In accordance with another embodiment, the present invention provides a method for diagnosing a disease or condition in a subject, the method comprising: (a) comparing the N-linked glycan profile from a subject to an N-linked glycan profile from a normal sample or diseased sample; and (b) determining whether the subject has the disease or condition; wherein the glycan profile is determined by: (i) obtaining a biological sample comprising at least one glycoprotein; (ii) denaturing the at least one glycoprotein in the biological sample; (iii) releasing at least one glycan from the at least one glycoprotein; (iv) coating the biological sample with a matrix; (v) analyzing the at least one glycan using mass spectrometry; and wherein spatial distribution of the at least one glycan is maintained.

In accordance with still another embodiment, the present invention provide a method for improving the limit of detection of one or more target analytes in a sample, the method comprising: a) obtaining a sample; b) adding to the sample a known concentration of one or more target analytes; c) applying the sample to a matrix; d) analyzing the at least one target analyte using mass spectrometry wherein the limit of detection of the one or more target analytes is calculated using the formula Signal $(C+LOD_C)$=Signal $(C)+3SD_C$.

In accordance with yet another embodiment, the present invention provide a method for preserving and detecting sialic acid residues in a sample comprising: (a) obtaining a biological sample comprising at least one sialic acid containing glycoprotein; (b) adding p-toluidine to the sample; (c) denaturing the at least one sialic acid containing glycoprotein in the biological sample; (d) releasing at least one sialic acid containing glycan from the at least one sialic acid containing glycoprotein; (e) coating the biological sample with a matrix; (f) analyzing the at least one sialic acid containing glycan using mass spectrometry; and wherein spatial distribution of the at least one sialic acid containing glycan is maintained.

Certain aspects of the presently disclosed subject matter having been stated hereinabove, which are addressed in whole or in part by the presently disclosed subject matter, other aspects will become evident as the description proceeds when taken in connection with the accompanying Examples and Figures as best described herein below.

BRIEF DESCRIPTION OF THE DRAWINGS

FIG. 7 shows that labeling the sialylated N-glycans with P-toluidine protects them in MALD-MS.

FIG. 10 shows MALDI-MS imaging to directly profile and image linked glycans from FFPE tissue sections (top) and in situ chemical labeling of tissue sections to image FFPE tissue sections (bottom).

DETAILED DESCRIPTION OF THE INVENTION

Figure 1:
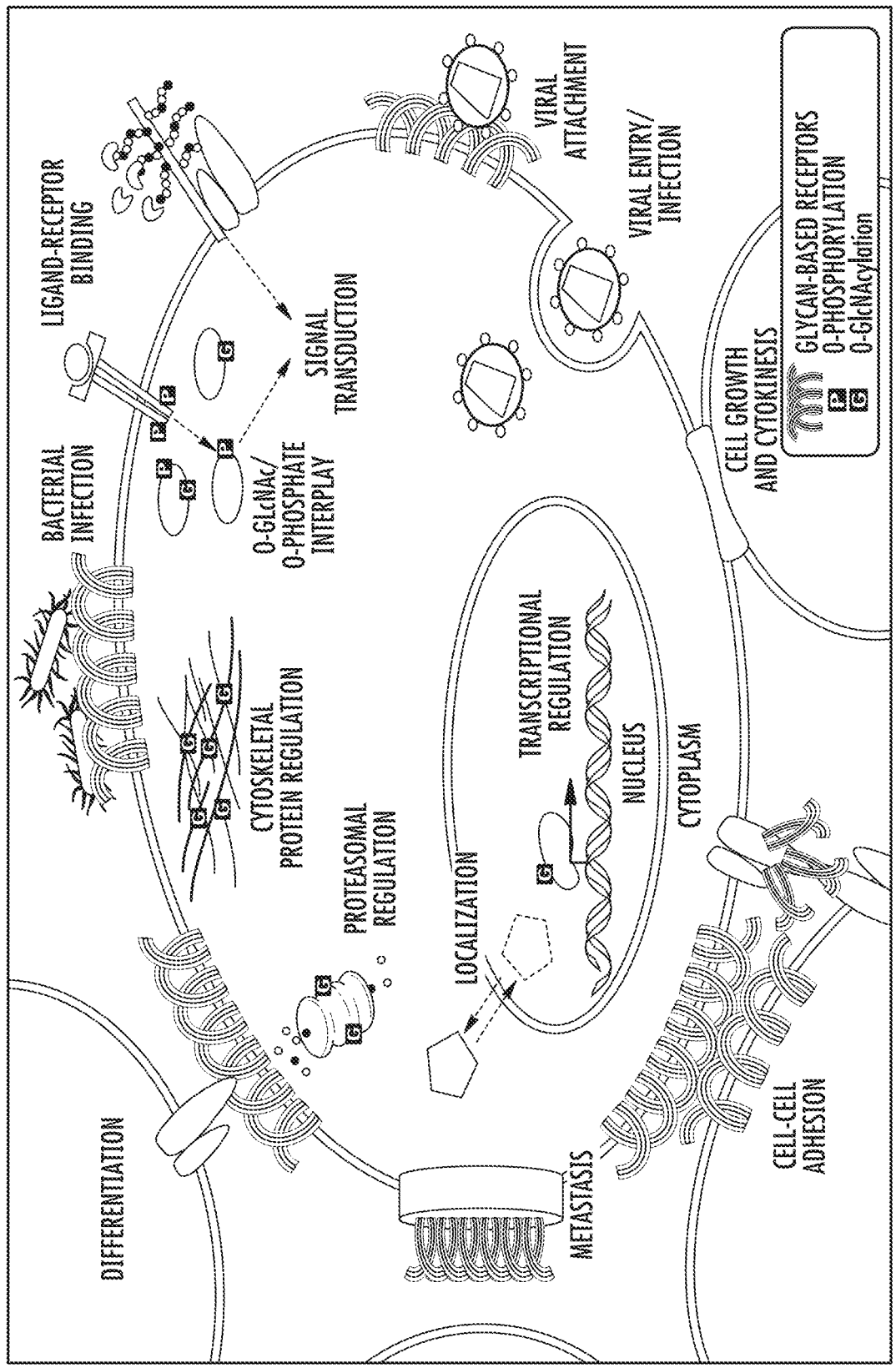
FIG. 1 shows that glycans play multi-faceted roles in many biological processes.
Figure 2:
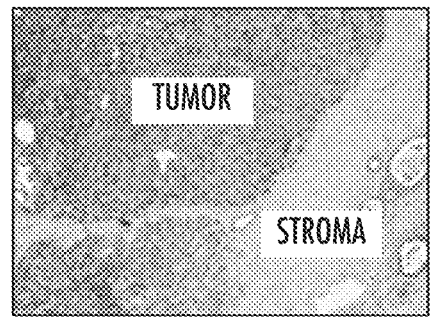
FIG. 2 shows the glycan imaging methods known in the art for FFPE tissue sections (Prior Art).

Methods are provided herein which are directed to improved methods of analyzing various target analytes including, for example, proteins, peptides and carbohydrates. As used herein, the term "carbohydrate" is intended to include any of a class of aldehyde or ketone derivatives of polyhydric alcohols. Therefore, carbohydrates include starches, celluloses, gums and saccharides. Although, for illustration, the term "saccharide" or "glycan" is used below, this is not intended to be limiting. It is intended that the methods provided herein can be directed to any carbohydrate, and the use of a specific carbohydrate is not meant to be limiting to that carbohydrate only.

The terms "sample," "patient sample," "biological sample," and the like, encompass a variety of sample types obtained from a patient, individual, or subject and can be used in a diagnostic, prognostic or monitoring assay. The patient sample may be obtained from a healthy subject, a diseased patient including, for example, a patient having associated symptoms of SWS, KTWS or PWS. Moreover, a sample obtained from a patient can be divided and only a portion may be used for diagnosis, prognosis or monitoring. Further, the sample, or a portion thereof, can be stored under conditions to maintain sample for later analysis. The definition specifically encompasses blood and other liquid samples of biological origin (including, but not limited to, peripheral blood, serum, plasma, urine, saliva, amniotic fluid, stool and synovial fluid), solid tissue samples such as a biopsy specimen or tissue cultures or cells derived therefrom and the progeny thereof. In a specific embodiment, a sample comprises a skin sample. In another embodiment, a sample of brain tissue is used. In other embodiments, a sample comprises a blood or serum sample. The definition also includes samples that have been manipulated in any way after their procurement, such as by centrifugation, filtration, precipitation, dialysis, chromatography, treatment with reagents, washed, or enriched for certain cell populations. The terms further encompass a clinical sample, and also include cells in culture, cell supernatants, tissue samples, organs, and the like. Samples may also comprise fresh-frozen and/or formalin-fixed, paraffin-embedded tissue blocks, such as blocks prepared from clinical or pathological biopsies, prepared for pathological analysis or study by immunohistochemistry.

The terms "providing a sample" and "obtaining a biological (or patient) sample" are used interchangeably and mean to provide or obtain a biological sample for use in methods described in this invention. Most often, this will be done by removing a sample of cells from a patient, but can also be accomplished by using previously isolated cells (e.g., isolated by another person, at another time, and/or for another purpose), or by performing the methods of the invention in vivo. Archival tissues, having treatment or outcome history, can also be used.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers, those containing modified residues, and non-naturally occurring amino acid polymer.

The term "amino acid" refers to naturally occurring and synthetic amino acids, as well as amino acid analogs and amino acid mimetics that function similarly to the naturally occurring amino acids. Naturally occurring amino acids are those encoded by the genetic code, as well as those amino acids that are later modified, e.g., hydroxyproline, .gamma.-carboxyglutamate, and O-phosphoserine. Amino acid analogs refers to compounds that have the same basic chemical structure as a naturally occurring amino acid, e.g., an .alpha. carbon that is bound to a hydrogen, a carboxyl group, an amino group, and an R group, e.g., homoserine, norleucine, methionine sulfoxide, methionine methyl sulfonium. Such analogs may have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions similarly to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical or associated, e.g., naturally contiguous, sequences. Because of the degeneracy of the genetic code, a large number of functionally identical nucleic acids encode most proteins. For instance, the codons GCA, GCC, GCG and GCU all encode the amino acid alanine. Thus, at every position where an alanine is specified by a codon, the codon can be altered to another of the corresponding codons described without altering the encoded polypeptide. Such nucleic acid variations are "silent variations," which are one species of conservatively modified variations. Every nucleic acid sequence herein which encodes a polypeptide also describes silent variations of the nucleic acid. One of skill will recognize that in certain contexts each codon in a nucleic acid (except AUG, which is ordinarily the only codon for methionine, and TGG, which is ordinarily the only codon for tryptophan) can be modified to yield a functionally identical molecule. Accordingly, often silent variations of a nucleic acid which encodes a polypeptide is implicit in a described sequence with respect to the expression product, but not with respect to actual probe sequences.

As to amino acid sequences, one of ordinary skill in the art recognizes that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention. Typical conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)).

As used herein, the term "saccharide" refers to a polymer comprising one or more monosaccharide groups. Saccharides, therefore, include mono-, di-, tri- and polysaccharides (or glycans). Glycans can be branched or branched. Glycans can be found covalently linked to non-saccharide moieties, such as lipids or proteins (as a glycoconjugate). These covalent conjugates include glycoproteins, glycopeptides, peptidoglycans, proteoglycans, glycolipids and lipopolysaccharides. The use of any one of these terms also is not intended to be limiting as the description is provided for illustrative purposes. In addition to the glycans being found as part of a glycoconjugate, the glycans can also be in free form (i.e., separate from and not associated with another moiety). The use of the term peptide is not intended to be limiting. The methods provided herein are also intended to include proteins where "peptide" is recited.

In some embodiments, the methods are methods of diagnosis and the pattern is associated with a diseased state. In one preferred embodiment, the pattern associated with a diseased state is a pattern associated with cancer, such as prostate cancer, melanoma, bladder cancer, breast cancer, lymphoma, ovarian cancer, lung cancer, colorectal cancer or head and neck cancer. In other preferred embodiments, the pattern associated with a diseased state is a pattern associated with an immunological disorder; a neurodegenerative disease, such as a transmissible spongiform encephalopathy, Alzheimer's disease or neuropathy; inflammation; rheumatoid arthritis; cystic fibrosis; or an infection, preferably viral or bacterial infection. In other embodiments, the method is a method of monitoring prognosis and the known pattern is associated with the prognosis of a disease. In yet another embodiment, the method is a method of monitoring drug treatment and the known pattern is associated with the drug treatment. In particular, the methods (e.g., analysis of glycome profiles) are used for the selection of population-oriented drug treatments and/or in prospective studies for selection of dosing, for activity monitoring and/or for determining efficacy endpoints.

Methods of analyzing glycans of glycoconjugates can also include cleaving the glycans from glycoconjugates using a releasing agent. A releasing agent can comprise any chemical or enzymatic methods or combinations thereof that are known in the art. An example of a chemical method for cleaving glycans from glycoconjugates is hydrazinolysis or alkali borohydrate. Enyzmatic methods include methods that are specific to N- or O-linked sugars. These enzymatic methods include the use of Endoglycosidase H (Endo H), Endoglycosidase F (EndoF), N-Glycanase F (PNGaseF) or combinations thereof. In some preferred embodiments, PNGaseF is used when the release of N- glycans is desired. When PNGaseF is used for glycan release the proteins is, for example, first unfolded prior to the use of the enzyme. The unfolding of the protein can be accomplished with any of the denaturing agents provided above.

Mass spectrometry imaging (MSI) is a powerful tool that has been used to correlate various peptides, proteins, lipids and metabolites with their underlying histopathology in tissue sections. Taking advantage of the rapid advances in mass spectrometry, MSI can push the limits of glycomics studies. Mass spectrometry imaging offers some advantages over the conventional methods that support its use as a complementary technique to lectin histochemistry. One significant advantage is that MALDI imaging combined with tandem mass spectrometry reveals detailed structural information about the glycans in a sample. A wide range of molecular weights can be detected by mass spectrometry imaging. Also, the high mass resolution allows distinguishing two peaks with close molecular weights, which subsequently improves the detection specificity. In addition, tens or even hundreds of glycans can be detected at femtomole levels in one single image, allowing detection of low concentrations of molecules. Therefore, MALDI imaging facilitates high-throughput analysis of tissue glycans. MALDI imaging can also be used for performing quantitative assays. Another significant advantage of MALDI imaging is that it has the capability of detecting an unknown compound without any a priori knowledge of the analytes. Therefore, this technique is particularly suitable for biomarker discovery research.

Matrix-assisted laser desorption/ionization (MALDI) is a soft ionization mass spectrometric technique that is suitable for use in the analysis of biomolecules, such as proteins, peptides, sugars, and the like, which tend to be fragile and fragment when ionized by conventional ionization methods.

Generally, MALDI comprises a two-step process. In the first step, desorption is triggered by an ultraviolet (UV) laser beam. The matrix material absorbs the UV laser radiation, which leads to the ablation of an upper layer of the matrix material, thereby producing a hot plume. The hot plume contains many species: neutral and ionized matrix molecules, protonated and deprotonated matrix molecules, matrix clusters, and nanodroplets. In the second step, the analyte molecules are ionized, e.g., protonated or deprotonated, in the hot plume.

The matrix material comprises a crystallized molecule capable of absorbing the UV laser radiation. Common matrix materials include, but are not limited to, 3,5-dimethoxy-4-hydroxycinnamic acid (sinapinic acid), CHCA, and DHB. A solution of the matrix material is made, either in highly purified water and an organic solvent, such as acetonitrile or ethanol. In some embodiments, a small amount of trifluoroacetic acid (TFA) also can be added to the solution.

The matrix solution can then be mixed with the analyte, e.g., a protein sample. This solution is then deposited onto a MALDI plate, wherein the solvents vaporize leaving only the recrystallized matrix comprising the analyte molecules embedded in the MALDI crystals.

The type of mass spectrometer typically used with MALDI is the time-of-flight (TOF) mass spectrometer, which has a large mass range. In accordance with one or more embodiments of the present invention, the mass spectrometric method comprises MALDI-TOF. In particular embodiments, the mass spectrometric method comprises MALDI-TOF tandem mass spectrometry. In yet another embodiment, mass spectrometry can be combined with another appropriate method(s) as may be contemplated by one of ordinary skill in the art, for example, HPLC, or LC/MS and the like.

In accordance with one or more embodiments of the present invention, the mass spectrometry comprises a MALDI- quadrupole ion trap (QIT)-TOF mass spectrometer, which, in some embodiments, can include a tandem mass spectrometer system. Such mass spectrometer systems provide for the structural characterization of biomolecules, not only their mass measurement. Such systems provide multiple advantages for characterizing biomolecules including, but not limited to, time of flight resolution and accuracy independent of laser energy applied and a wide mass range of ions trapped (up to 20 kDa). Such systems can comprise a MALDI plate, an ion trap, a reflectron and a detector.

In accordance with an embodiment, the present invention provides a MSI technique that has been developed for direct profiling of N-linked glycans from formalin-fixed paraffin-embedded (FFPE) tissues. FFPE tissues are sectioned on indium tin oxide coated glass slides for matrix-assisted laser desorption/ionization mass spectrometry (MALDI-MS). Deparaffinization and rehydration of the tissue sections are followed by antigen retrieval and denaturing of the proteins. A releasing agent, such as Peptide-N-Glycosidase F (PNGase F), can be sprayed over the tissue sections to release the N-linked glycans from the proteins, while preserving their spatial distribution. Samples can then be spray-coated with matrix and analyzed by MALDI-MS-MS2-MSn (Shimadzu Axima Resonance in positive mode).

In accordance with another embodiment, the present invention provides a method for direct profiling of N-linked glycans in a biological sample, the method comprising: (a) obtaining a biological sample comprising at least one glycoprotein; (b) denaturing the at least one glycoprotein in the biological sample; (c) releasing at least one glycan from the at least one glycoprotein; (d) coating the biological sample with matrix; and (e) analyzing the at least one glycan using mass spectrometry; and wherein spatial distribution of the at least one glycan is maintained.

In some embodiments, the biological sample is a paraffin-embedded tissue and/or formalin-fixed tissue. In still another embodiment, the biological sample is rehydrated. In a further embodiment, the biological sample is deposited on a solid support.

It will be understood by those of skill in the art that for spatial distribution of the glycans in the biological sample to be maintained, a solid support, such as a glass plate or slide, or similar support, can be used with sectioning. In some embodiments, a biological sample, such as a tissue, is raster scanned by a laser in the x and y directions and mass spectra are acquired for each pixel on the tissue.

In accordance with another embodiment, the denaturation of the glycoprotein(s) occurs by heating the biological sample and/or incubating the biological sample with a proteolytic enzyme for a sufficient period of time.

In accordance with still another embodiment, releasing the N-linked glycan(s) on the glycoprotein(s) occurs by using a releasing agent, for example, Peptide-N-Glycosidase F (PNGase F). In further embodiments, releasing the glycan(s) occurs by using a microarray printer in combination with a releasing agent.

In still further embodiments, a matrix is used, such as 2,5-dihydroxybenzoic acid (DHB). In particular embodiments, the mass spectrometry method used is MALDI-mass spectrometry.

In accordance with an embodiment, the present invention also provides a generic technique for improving the sensitivity and detection limit of MALDI-MS. This method, named targeted analyte detection (TAD), selectively enhances the detection of analytes (target molecules) of interest, such as proteins, peptides, and glycans, for example. In TAD, a small known amount of analyte of interest is spiked into the sample, thereby elevating the concentration to levels above the noise, where the interference of the noise is relatively reduced and the sensitivity is increased. The added analyte acts as a carrier to suppress the matrix effect (introduced by interferences with other compounds in the sample) and enhances ion abundance of analyte of interest. The measured signal is thus contributed by both the endogenous and exogenous (spiked-in) analytes. Therefore, TAD uses the added standard to reveal the endogenous target analyte that was otherwise buried in the noise.

As disclosed herein, the feasibility of TAD in improving the detection limit of MALDI-MS is presented. Additionally, the present invention also provides a systematic method for optimizing the spiking amount needed to achieve the maximum improvement in the limit of detection (LOD). The main advantage of TAD is that it is not limited to certain types of analytes, provided that the analyte of interest is available or can be synthesized for spiking into the unknown sample. Furthermore, this approach takes advantage of the generic sigmoidal shape of the calibration curve, which is very reproducible in a wide range of analytical instruments. Therefore, this method might be capable of improving the sensitivity in a wide range of instruments regardless of the detection technologies, including but not limited to mass spectrometers.

Figure 11:
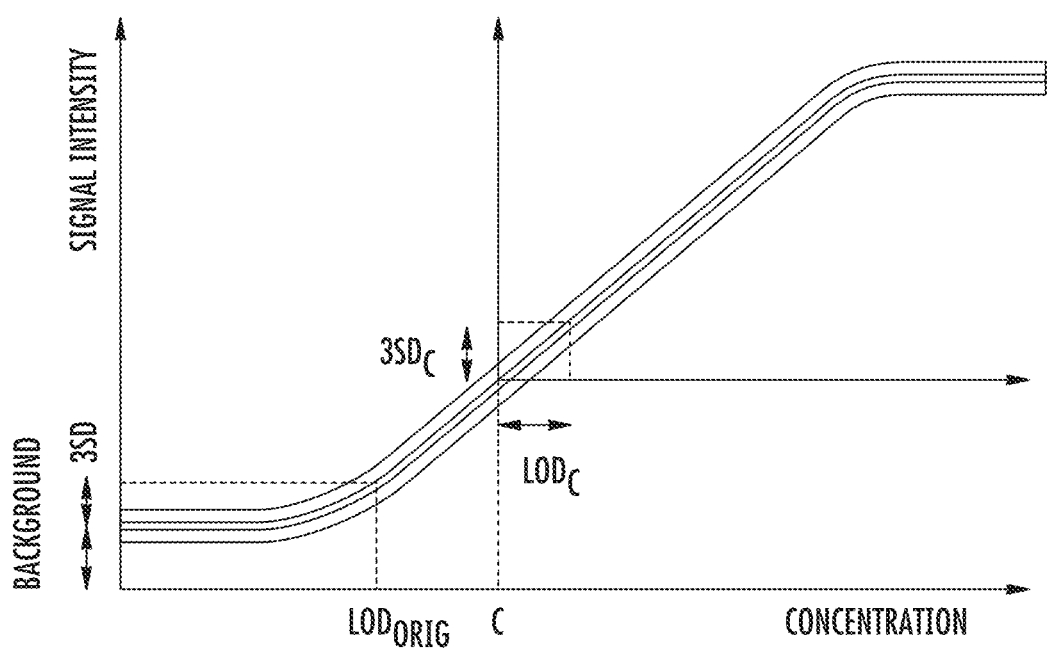
FIG. 11 depicts presence of background, limited dynamic range, limit of detection, limited detection efficiency and variations cause the deviation between the realistic calibration curve from the ideal curve where the signal is proportional to the analyte concentration. Shifting the reference point to the linear dynamic range of the calibration curve will enhance the sensitivity and improve the LOD by spiking in certain exogenous concentrations of target analyte. The original calibration curve of the analyte of interest is used for this estimation of the predicted LODC. The reference point for calculation of LODC is shifted to the given exogenous concentration.

Estimation of LOD. A code was developed to estimate the predicted LOD. The mean and standard deviation of the measurements for the control group without TAD solution was used as the input to the code. For each target analyte, the original LOD was calculated based on the commonly used definition of LOD as shown in eq 1:

$$\text{Signal (LOD}_{orig}) = \text{Signal (Background)} + 3\text{SD}, \quad (1)$$

where $\text{LOD}_{orig}$ is the limit of detection in the absence of any exogenous target analyte and Signal ($\text{LOD}_{orig}$) is the total signal at this concentration. Signal (Background) represents the background signal mean and SD denotes the background signal standard deviation (FIG. 11).

For a given exogenous concentration of the target peptide in TAD solution, the LOD was estimated by shifting the reference point of the background to the given exogenous spiking peptide concentration (C) used in TAD solution. The signal and standard deviation at any concentration were estimated by interpolating the signal and standard deviation of the calibration curve without exogenous peptide in TAD solution, respectively. Denote the limit of detection at the spiking concentration C fmol/µL of the target analyte in the TAD solution, as $\text{LOD}_C$ and $\text{LOD}_C$ should then satisfy eq 2:

$$\text{Signal (C+LOD}_C) = \text{Signal (C)} + 3\text{SD}_C. \quad (2)$$

It is noted that for the control set with no spiking target peptide in the TAD solution, C is set to zero (FIG. 1 and eq 1).

Ideally, the measured signal for each analyte is proportional to the amount of that analyte in the sample. However, the detection accuracy is compromised by factors such as background, detection efficiency, sample preparation and signal detection variations, and the limit of detection in mass spectrometry. Presence of background results in a nonzero signal even at zero concentration of the analyte. Suboptimal detection efficiency compromises the output signal. Analyte concentration variations introduced by analyte-matrix cocrystallization, desorption/ionization, analyzer and detector add noise to the measurements, thus limiting the threshold as well as the confidence of low abundance analyte detection.

Figure 12:
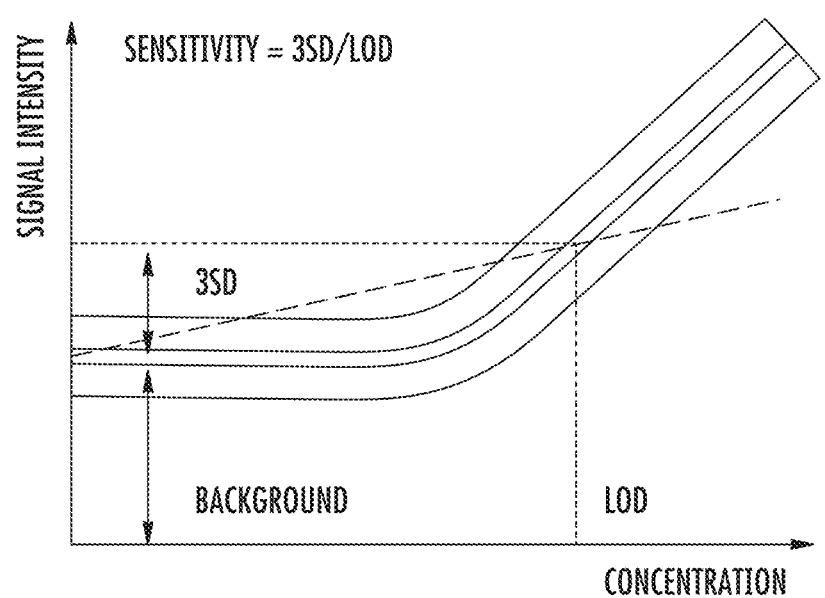
FIG. 12 shows the correlation between the LOD, sensitivity and the standard deviation is depicted. The slope of the dotted line is by definition the average sensitivity over the concentration range from 0 to LOD. On the other hand, this slope equals three times the standard deviation divided by LOD. Therefore, LOD is proportional to the SD divided by the sensitivity.

Therefore, in accordance with some embodiments, the practical calibration curve of MALDI-MS, which is the measured mass spectral signal versus a given analyte concentration, differs from the ideal curve in crucial aspects (FIG. 11). The sigmoidal shape of the practical calibration curve arises from these differences, whereas the signal intensity is linearly proportional to the analyte concentration in the ideal curve. LOD corresponds to the concentration of an analyte that produces a signal at least as large as the background mean plus three times the background standard deviation. Thus, the LOD can be estimated by the standard deviation of the background as well as the sensitivity, based on eq 3 (FIG. 12):

$$\text{LOD} = 3\text{SD/Sensitivity}, \quad (3)$$

where sensitivity is defined as the slope of the calibration curve. Eq 3 indicates that LOD is directly proportional to the standard deviation and inversely proportional to the sensitivity; therefore, lower noise level and higher sensitivity improve the LOD. This provides the opportunity that one can improve the LOD by improving the reproducibility or sensitivity.

In accordance with one or more embodiments, the methods of the present invention allow direct imaging of glycans on tissues to determine disease-specific glycosylation changes. Therefore, in some embodiments, these methods provide a method of diagnosing a disease or condition in a subject comprising: (a) comparing the N-linked glycan profile from a subject to an N-linked glycan profile from a normal sample or diseased sample; (b) determining whether the subject has the disease or condition; and wherein the glycan profile is determined using the presently disclosed methods. In other embodiments, the disease or disorder is a cancer.

It will be understood by those of ordinary skill in the art that other diseases or conditions in which aberrant glycoproteins are indicative can be identified using the inventive methods provided herein.

In accordance with one or more embodiments, the presently disclosed methods detect glycoproteins, glycoprotein biomarkers, and/or aberrant glycans by tissue glycan imaging. In other embodiments, therapeutic targets can be identified by the presently disclosed methods by identifying aberrant glycans.

In further embodiments, diagnostic kits comprising instructions and materials that can be used to perform the presently disclosed methods also are provided.

As stated above, the glycosylation of a protein may be indicative of a normal or a disease state. Therefore, methods are provided for diagnostic purposes based on the analysis of the glycosylation of a protein or set of proteins, such as the total glycome. The methods provided herein can be used for the diagnosis of any disease or condition that is caused or results in changes in a particular protein glycosylation or pattern of glycosylation. These patterns can then be compared to "normal" and/or "diseased" patterns to develop a diagnosis, and treatment for a subject. For example, the methods provided can be used in the diagnosis of cancer, inflammatory disease, benign prostatic hyperplasia (BPH), etc.

The diagnosis can be carried out in a person with or thought to have a disease or condition. The diagnosis can also be carried out in a person thought to be at risk for a disease or condition. "A person at risk" is one that has either a genetic predisposition to have the disease or condition or is one that has been exposed to a factor that could increase his/her risk of developing the disease or condition.

Detection of cancers at an early stage is crucial for its efficient treatment. Despite advances in diagnostic technologies, many cases of cancer are not diagnosed and treated until the malignant cells have invaded the surrounding tissue or metastasized throughout the body. Although current diagnostic approaches have significantly contributed to the detection of cancer, they still present problems in sensitivity and specificity.

In accordance with one or more embodiments of the present invention, it will be understood that the types of cancer diagnosis which may be made, using the methods provided herein, is not necessarily limited. For purposes herein, the cancer can be any cancer. As used herein, the term "cancer" is meant any malignant growth or tumor caused by abnormal and uncontrolled cell division that may spread to other parts of the body through the lymphatic system or the blood stream.

The cancer can be a metastatic cancer or a non-metastatic (e.g., localized) cancer. As used herein, the term "metastatic cancer" refers to a cancer in which cells of the cancer have metastasized, e.g., the cancer is characterized by metastasis of a cancer cells. The metastasis can be regional metastasis or distant metastasis, as described herein.

The terms "treat," and "prevent" as well as words stemming therefrom, as used herein, do not necessarily imply 100% or complete treatment or prevention. Rather, there are varying degrees of treatment or prevention of which one of ordinary skill in the art recognizes as having a potential benefit or therapeutic effect. In this respect, the inventive methods can provide any amount of any level of diagnosis, staging, screening, or other patient management, including treatment or prevention of cancer in a mammal. Furthermore, the treatment or prevention provided by the inventive method can include treatment or prevention of one or more conditions or symptoms of the disease, e.g., cancer, being treated or prevented. Also, for purposes herein, "prevention" can encompass delaying the onset of the disease, or a symptom or condition thereof.

In accordance with an embodiment, the present invention provides a use of a glycan profile prepared using the method disclosed herein to diagnose a disease or condition in a subject, comprising comparing the glycan profile from a subject to a glycan profile from a normal sample, or diseased sample, and determining whether the sample of the subject has the disease or condition. Examples of non-cancer related diseases or disorders include congenital disorders of glycosylation, such as failure to thrive, mental retardation, hypotonia, hypoglycemia, cerebellar hypoplasia, liver dysfunction, coagulopathy, partial TBG deficiency, perinatal dysmorphia, microcephaly, loose wrinkled skin, skeletal anomalies, short stature, recurrent infections, thrombocytopenia, neutropenia, seizures and stroke-like episodes, and dandy-walker malformation.

In accordance with the inventive methods, the terms "cancers" or "tumors" also include but are not limited to adrenal gland cancer, biliary tract cancer; bladder cancer, brain cancer; breast cancer; cervical cancer; choriocarcinoma; colon cancer; endometrial cancer; esophageal cancer; extrahepatic bile duct cancer; gastric cancer; head and neck cancer; intraepithelial neoplasms; kidney cancer; leukemia; lymphomas; liver cancer; lung cancer (e.g. small cell and non-small cell); melanoma; multiple myeloma; neuroblastomas; oral cancer; ovarian cancer; pancreas cancer; prostate cancer; rectal cancer; sarcomas; skin cancer; small intestine cancer; testicular cancer; thyroid cancer; uterine cancer; urethral cancer and renal cancer, as well as other carcinomas and sarcomas.

Although specific terms are employed herein, they are used in a generic and descriptive sense only and not for purposes of limitation. Unless otherwise defined, all technical and scientific terms used herein have the same meaning as commonly understood by one of ordinary skill in the art to which this presently described subject matter belongs.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, parameters, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments, ±100% in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The synthetic descriptions and specific examples that follow are only intended for the purposes of illustration, and are not to be construed as limiting in any manner to make compounds of the disclosure by other methods.

Example 1

Figure 3:
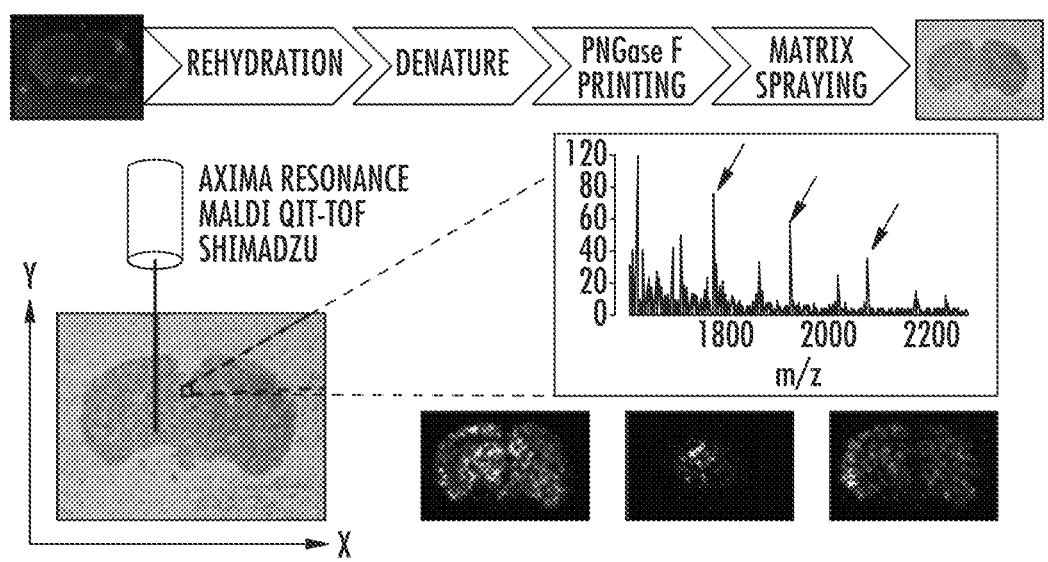
FIG. 3 shows mass spectrometry imaging of N-linked glycans on FFPE tissue sections.

Mass spectrometry imaging of glycans from tissue section. FIG. 3 shows a representative schematic of an imaging platform using the inventive methods. A FFPE tissue section is rehydrated, the proteins in the tissue section are denatured, and microarray printing using the release agent PNGase F is allowed to occur. PNGase F is the enzyme that cleaves N-linked glycans from their host proteins. To preserve the spatial distribution of the glycans, a microarray printer can be used to apply the PNGase F on the tissue in a grid. Then, a matrix, such as 2,5-dihydroxybenzoic acid (DHB), can be sprayed over the tissue using an airbrush. The tissue can then be analyzed with a mass spectrometer (Axima Resonance MALDI QIT-TOF, Shimadzu). One difference between a conventional MALDI analysis and the methods of the present invention is that the tissue is raster scanned by the laser in the x and y directions and mass spectra are acquired for each pixel on the tissue. At this point, by mapping the intensity of various peaks as a function of location, ion images can be generated for each glycan structure detected in the mass spectra.

Figure 4:
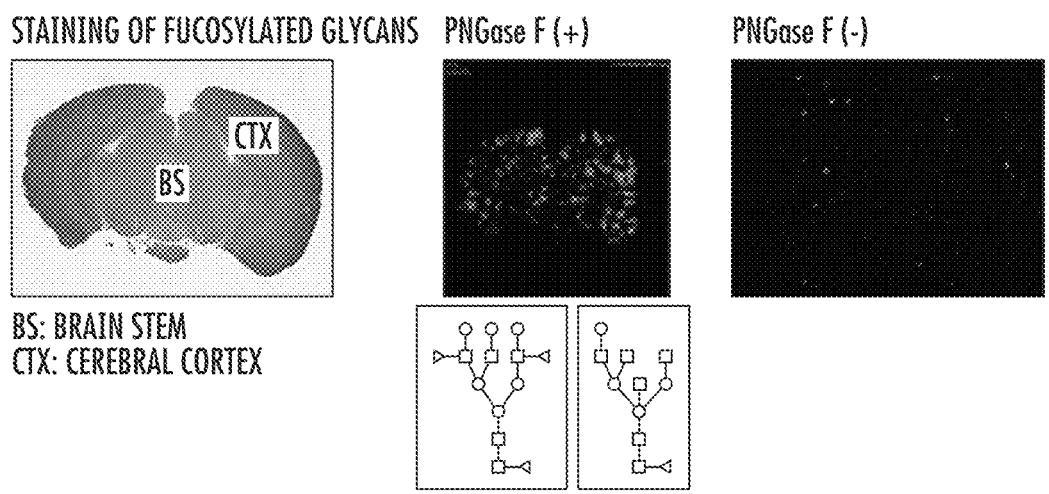
FIG. 4 shows coronal mouse brain tissue sections are imaged with and without PNGase F printing. PNGase F releases the N-linked glycans from FFPE sections for MALDI-MS imaging (the brain stem comprises the interbrain, midbrain, and hindbrain; mostly the midbrain is shown in this figure).

The methods of the present invention were used to analyze mouse brain coronal sections (FIG. 4). On the left of FIG. 4, the tissue stained with AAL lectin is depicted, and the cerebral cortex and brain stem regions are marked. The AAL lectin binds to the fucosylated glycans. According to this image, although fucosylated glycans are distributed throughout the brain, they seem to be higher in abundance in the cerebral cortex compared to the midbrain in the brain stem. The middle panels shows the MALDI images for two glycan ions that are overlaid and the structures of the glycan ions are shown below the image. The red signal corresponds to a glycan, which is highly fucosylated and the green signal shows the distribution of glycans with only one fructose. On the right of FIG. 4, the ion images are shown for those same glycans for a tissue that is not treated with PNGase F. Therefore, the enzymatic deglycosylation results in releasing of glycans and their subsequent desorption and ionization with MALDI-MS.

Figure 5:
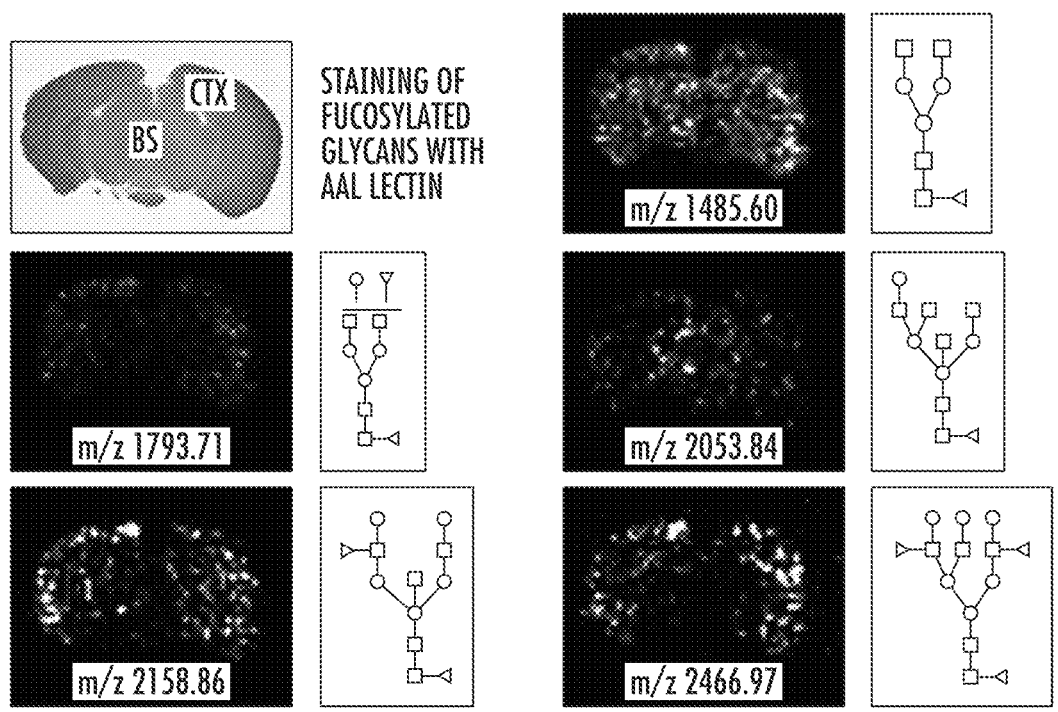
FIG. 5 shows ion images of fucosylated glycans on mouse brain coronal sections (CNU: cerebral nuclei; CTX: cerebral cortex; BS: brain stem).

FIG. 5 depicts ion images of some of the detected fucosylated glycans and these are compared with AAL lectin staining of an adjacent tissue section. Based on the AAL staining, fucosylation occurs in the cerebrum as well as brain stem, with a relatively higher abundance in the cerebral cortex. The ion images acquired from fucosylated glycan also show a similar pattern. With the exception of a glycan of 2053 Da, other glycans are either uniformly distributed over the tissue or have higher abundance in the cerebral cortex.

Figure 6:
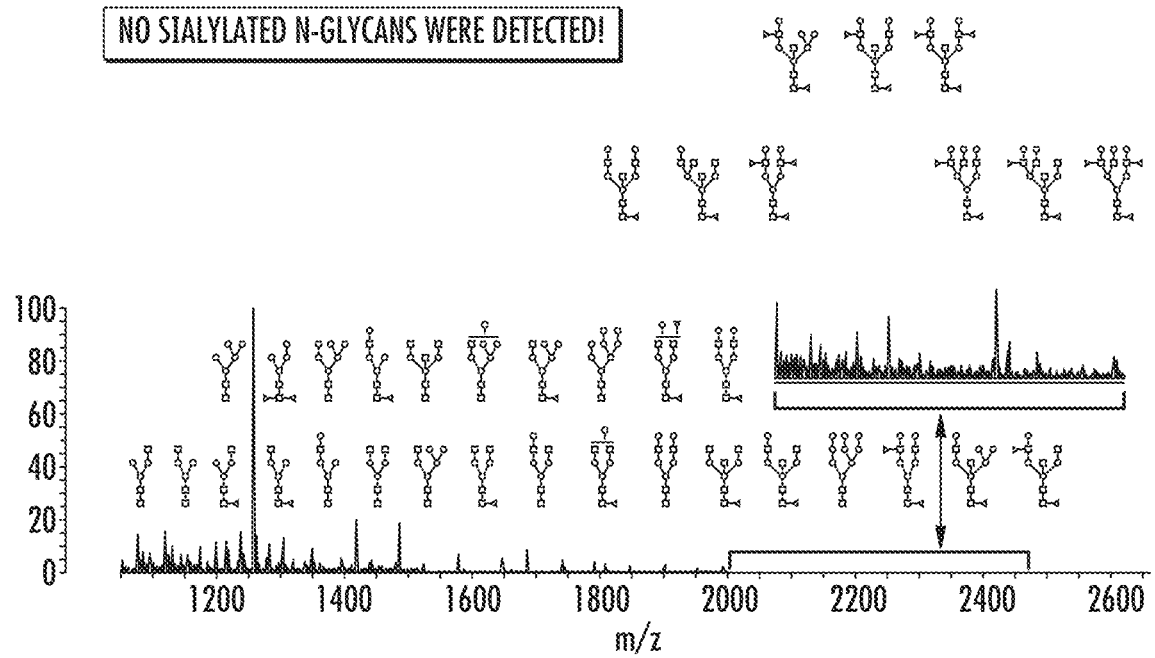
FIG. 6 shows glycans detected from PNGase F-printed mouse brain tissue section using MALDI-MS.

FIG. 6 shows the mass spectrum of the tissue section averaged over all tissue pixels. The identified glycans were compared with the functional glycomics database. Based on this comparison, approximately 72% of the mouse brain non-sialylated N-linked glycans were able to be detected. In this experiment, however, sialylated glycans were missing in this spectrum. Without wishing to be bound to any one particular theory, the missing sialylated glycans may be due to the loss of sialic acid during sample preparation or mass spectrometry analysis.

In accordance with some embodiments, the methods of the present invention were extended to image sialylated glycans from FFPE tissues as well (FIG. 7). Sialic acid is a terminal sugar residue on N-linked glycans shown by a diamond in glycan schematics. This sugar has proven to be challenging to analyze because it easily gets cut off from the glycans due to harsh sample preparation conditions or during post source decay MALDI-MS analysis. A technique for stabilizing the sialic acid residues in MALDI analysis by labeling them with p-toluidine was developed. Using these inventive methods, the labeled glycans, along with the non-sialylated glycans, are released from glycoprotein by enzymatic deglycosylation and analyzed with mass spectrometry.

Figure 8:
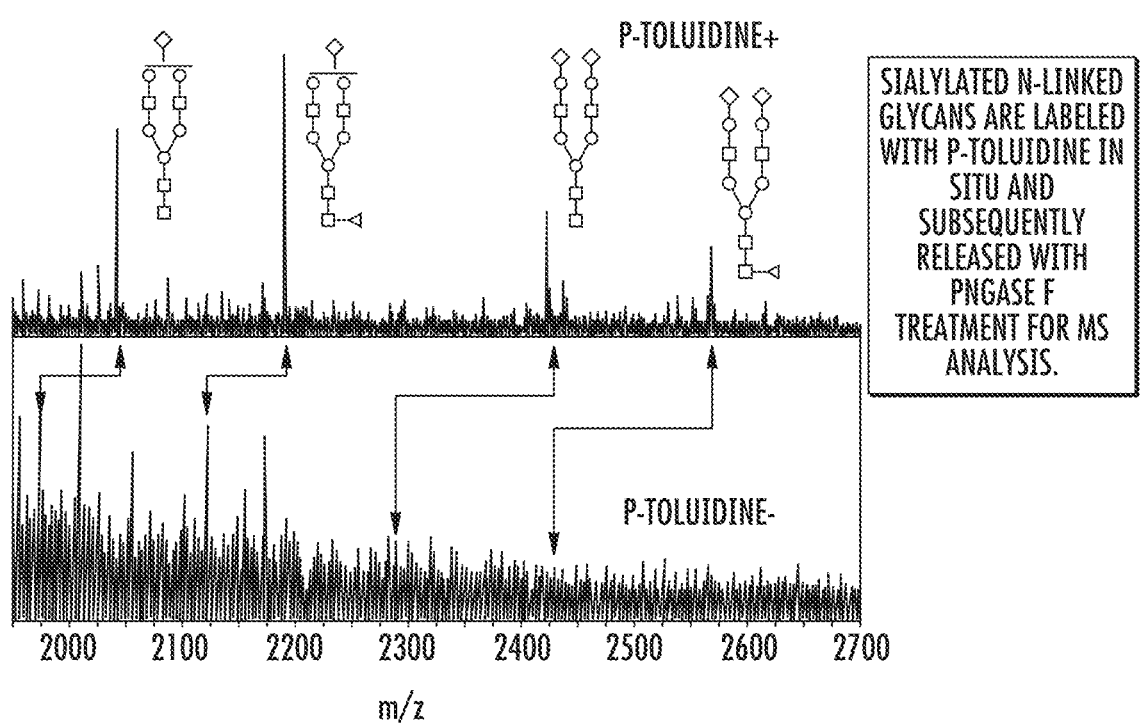
FIG. 8 shows that in situ P-toluidine labeling of sialylated glycans on FFPE tissues improves detection.

The new sialic acid protection methods of the present invention were tested on FFPE prostate tissue sections (FIG. 8). The mass spectrum on the upper panel shows the mass spectral peaks corresponding to sialylated glycans after in situ labeling with p-toluidine. By comparing these results with the control group, where no p-toluidine was applied, it was shown that this technique significantly improves the signal to noise ratio and detection of sialylated glycans.

Figure 9:
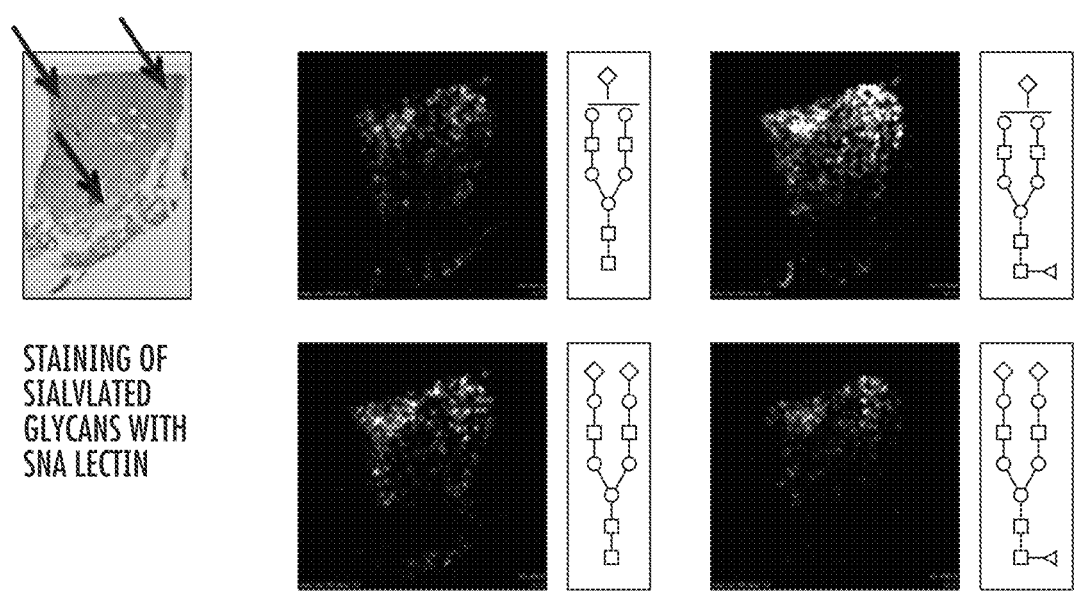
FIG. 9 shows imaging of sialylated N-linked glycans on prostate tissue sections.

FIG. 9 shows ion images of four sialylated glycans along with their structures. The histostaining with SNA lectin, which is used to stain sialylated glycans, showed a quite weak signal from sialylated glycans on tissue. Referring once again to FIG. 9, the sialylated glycans, even though they are low in abundance, were mostly located in the three regions marked by black arrows. Despite the low abundance of sialylated glycans and their weak staining in lectin histostaining images, the mass-spectrometry based detection was able to detect at least four sialylated glycans (FIG. 9).

The methods of the present invention provides release agent printing combined with MALDI mass spectrometry imaging to directly profile and image N-linked glycans from FFPE tissue sections (FIG. 10). In addition, in situ labeling of sialylated tissue glycans with p-toluidine was performed to image them on FFPE tissue sections.

Example 2

Figure 13A:
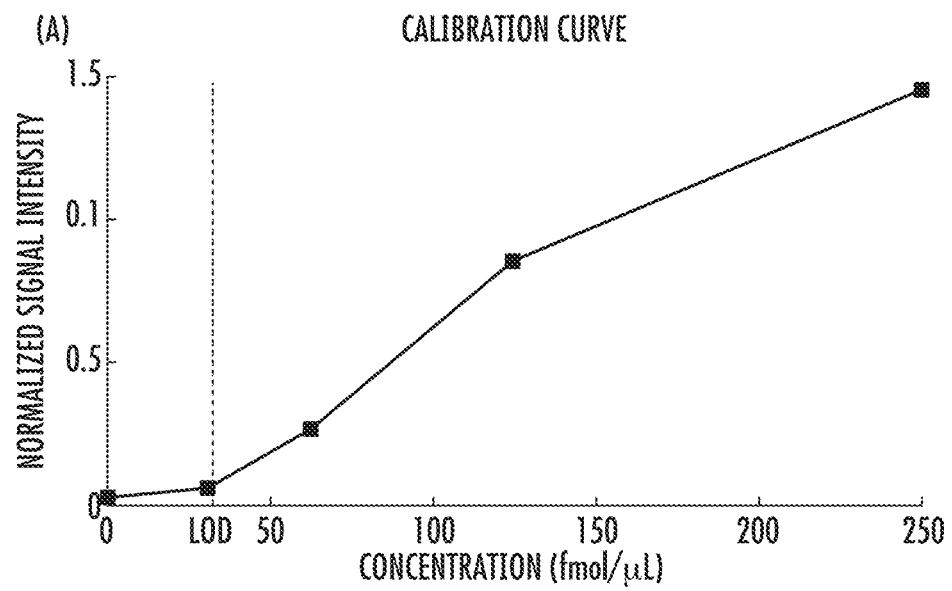
FIG. 13A-13D shows how sensitivity and standard deviation of the measurements change with the analyte concentration. A) Calibration curve for Angiotensin II generated using Applied Biosystems 4800 MALDI-TOF/TOF analyzer is depicted. B) Sensitivity sharply rises as the concentration increases to supra-LOD levels. C) The variation in standard deviation at low concentrations is modest compared to increments in the sensitivity. D) Coefficient of variation (CV) rapidly decreases from 40% at the background to ~5% for higher end of the curve. The LOD is marked by the vertical dashed line.
Figure 13B:
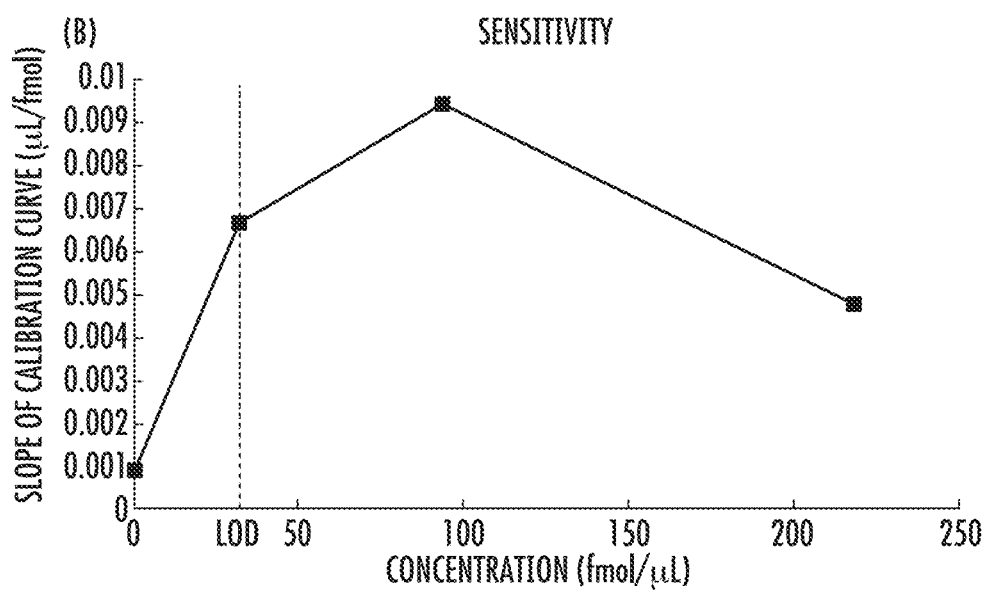
Figure 13C:
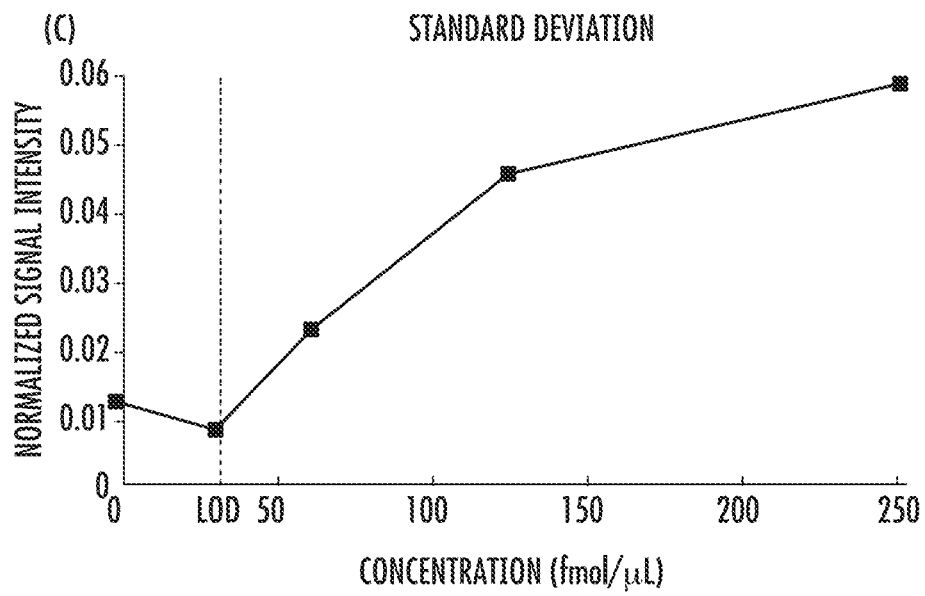
Figure 13D:
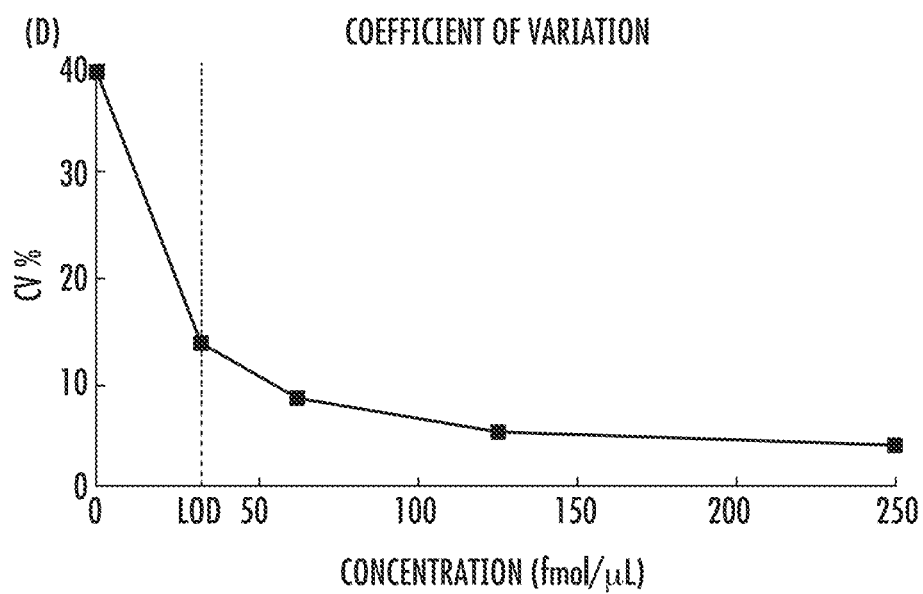

Concentration Dependent Sensitivity and SD. Sensitivity and standard deviation (SD) of an analyte greatly depend on the concentration of the target analyte in the sample. To illustrate the dependence, we calculated the sensitivity and SD versus analyte concentration using Angiotensin II as an example and the results are shown in (FIG. 13). The calibration curve of Angiotensin II was generated by analyzing sequential dilutions of this peptide with the mass spectrometer. The sensitivity was calculated from the calibration curve by dividing the signal difference by the concentration difference for two adjacent data points at each concentration. The standard deviation was computed from ten normalized mass spectral signals and is denoted as SD. Due to the sigmoidal shape of the calibration curve (FIG. 11 and FIG. 13A), the sensitivity, i.e. the slope of this curve stays stable at its maximum value over the linear range of the assay, and decreases as the concentration falls below the LOD or above the upper linear range (FIG. 11 and FIG. 13B). The standard deviations are usually modest at lower analyte concentration and increase with analyte concentration (FIG. 13C). Moreover, the coefficient of variation (CV) defined by the standard deviation divided by the signal mean also associated with the concentration of the target analyte and drops rapidly as the concentration of the analyte increases (FIG. 13D). As a result, there are certain concentrations of analyte with a lower SD to sensitivity ratio than this ratio at the background. These concentrations generally lie near the LOD of the target analyte, where the sensitivity increases dramatically (FIG. 11, FIGS. 13A and 13B), but SD still remains relatively low (FIG. 13C). Considering that the LOD depends on the ratio of SD to sensitivity, the LOD can then be improved by shifting the reference point of concentration to this range of a higher slope on the calibration curve by spiking additional analytes into the sample.

Example 3

Figure 14A:
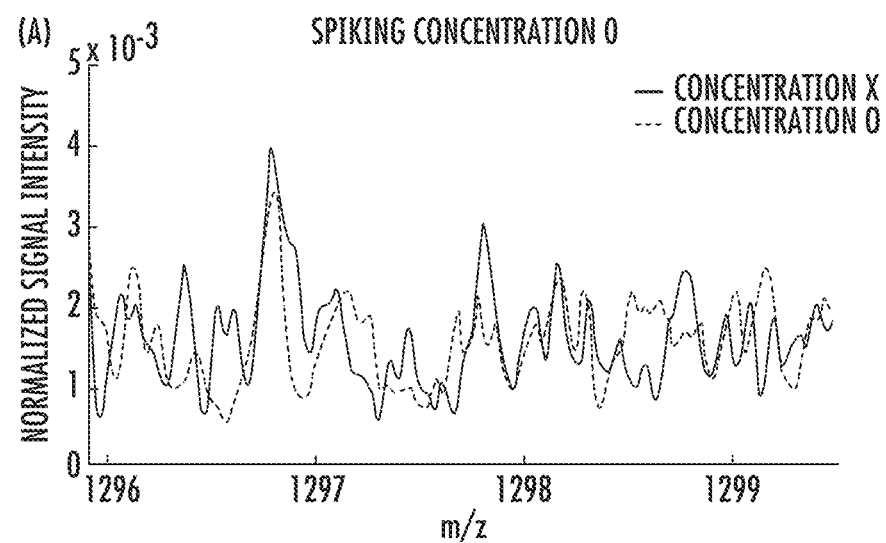
FIG. 14A-14B depicts the mass spectral peak of Angiotensin I ($m_a$=1296.685) at the reference point of LOD measurement (dotted line) and endogenous concentration X=31.25 fmol/µL (solid line) for A) control group, where C=0 and $LOD_{orig}$=64.5 fmol/µL and B) TAD experiment where C=50 fmol/µL and $LOD_C$=22.5 fmol/µL. A) In the control group, the solid line is hardly differentiated from the background. B) However, improving the LOD in the TAD experiment leads to significant distinction of the signal from the background at concentration X=31.25 fmol/µL. The peak intensities were normalized to the heavy isotope-peptide.
Figure 14B:
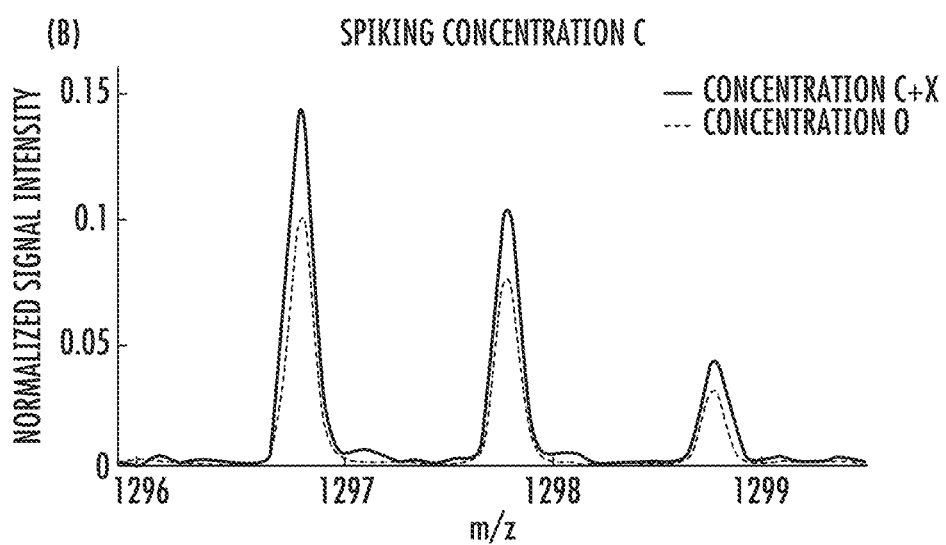

Determining LODs of Target Analytes in Simple Mixture. To determine whether the LOD could be lower with the target analytes spiked in TAD solution, we analyzed the target peptides in different dilutions in control solution (which did not have any spiking target peptides added) and in various TAD solutions (which had a different amount of target peptides spiked in the solution). The mass spectral peaks of Angiotensin I is depicted in FIG. 14 for the control and the TAD solution group. For this peptide, the measured $LOD_{orig}$ was 64.5 fmol/μL. Therefore, the mass spectral peak of Angiotensin I ($m_a$=1296.685), averaged over the ten measurements, is not distinguishable from the background at concentration of 31.25 fmol/μL (FIG. 14A). By spiking the target analyte with a concentration C=50 fmol/μL, the spectral signal is boosted and the LOD reduces to 22.5 fmol/μL. Consequently, as shown in FIG. 14B, the averaged mass spectral peak of Angiotensin I at the endogenous concentration of 31.25 fmol/μL and exogenous concentration of 50 fmol/μL (X=31.25 and C=50 fmol/μL, i.e. 81.25 fmol/μL) is significantly higher than the background at exogenous concentration of 50 fmol/μL.

Figure 15A:
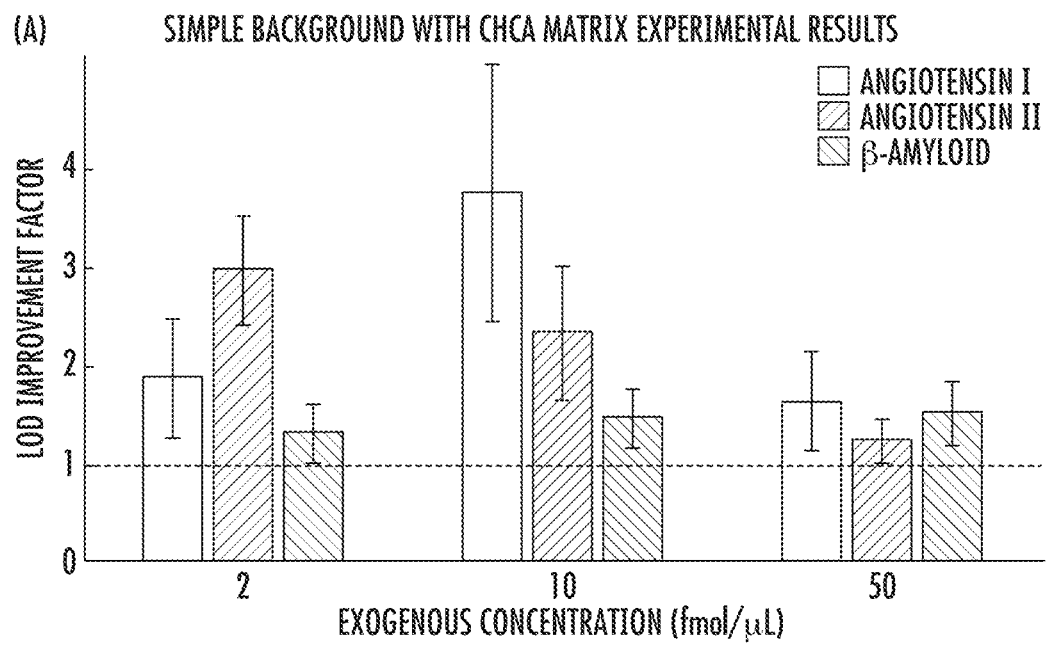
FIG. 15A-15B shows experimental improvement factors for three peptides in simple background are averaged over four replicates. A) When using α-cyano-4-hydroxycinnamic acid (CHCA), the LOD is improved in all of the 9 experimental pairs yielding improvement factors greater than 1. B) The LOD is improved in 8 of the 9 experimental pairs when 2,5-dihydroxybenzoic acid (DHB) is used as the MALDI matrix. The dotted line shows the threshold of LOD improvement. The error-bars show the standard error of the mean.
Figure 15B:
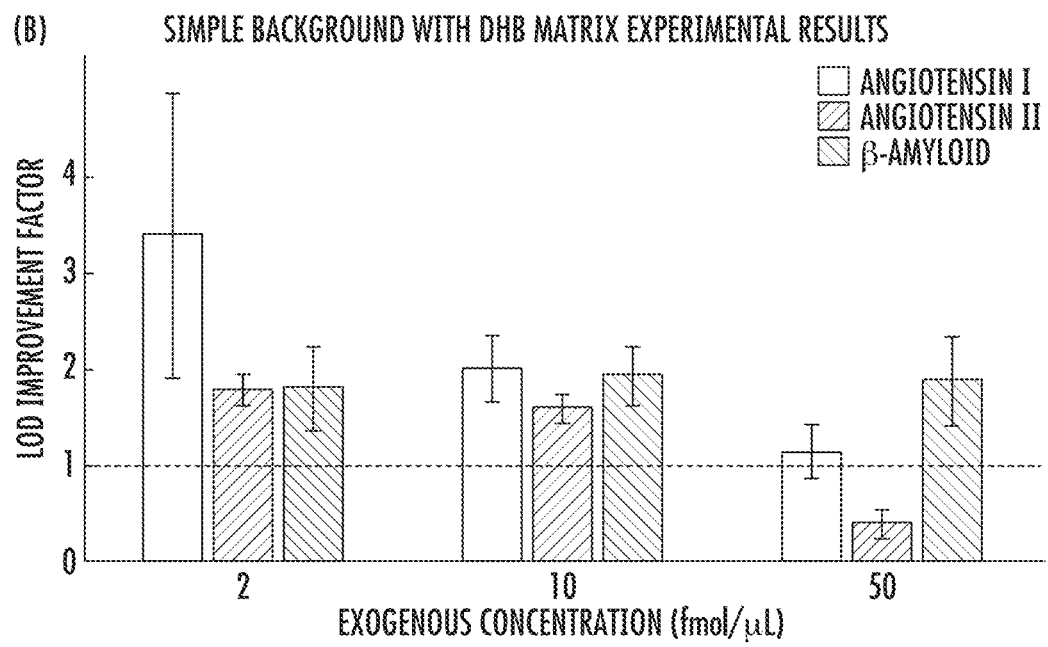

To determine whether this LOD improvement method and the dependence of the LOD improvement on the spiking target analyte concentration could be applicable to other analytes, three analytes, Angiotensin I, Angiotensin II, and β-Amyloid (1-15), with three different concentrations of target analytes spiked in TAD solution were tested. Nine experimental conditions (three exogenous concentrations for each of the three targeted peptides) were studied in four replicate measurements with independent sample preparation. The experiment was performed in both CHCA and DHB as the MALDI matrix. On average, in CHCA matrix, TAD successfully improved the LODs in all nine experimental conditions (FIG. 15A). TAD successfully improved the LODs in eight of nine experimental conditions when using DHB as matrix (FIG. 15B). Improvement factor is defined by $LOD_{orig}$ divided by $LOD_C$, where $LOD_{orig}$ is the LOD of the control group with no exogenous peptides spiked to the solution, and $LOD_C$ represents the LOD that was achieved by boosting the concentration by spiking the analyte of a concentration C fmol/μL.

Figure 16A:
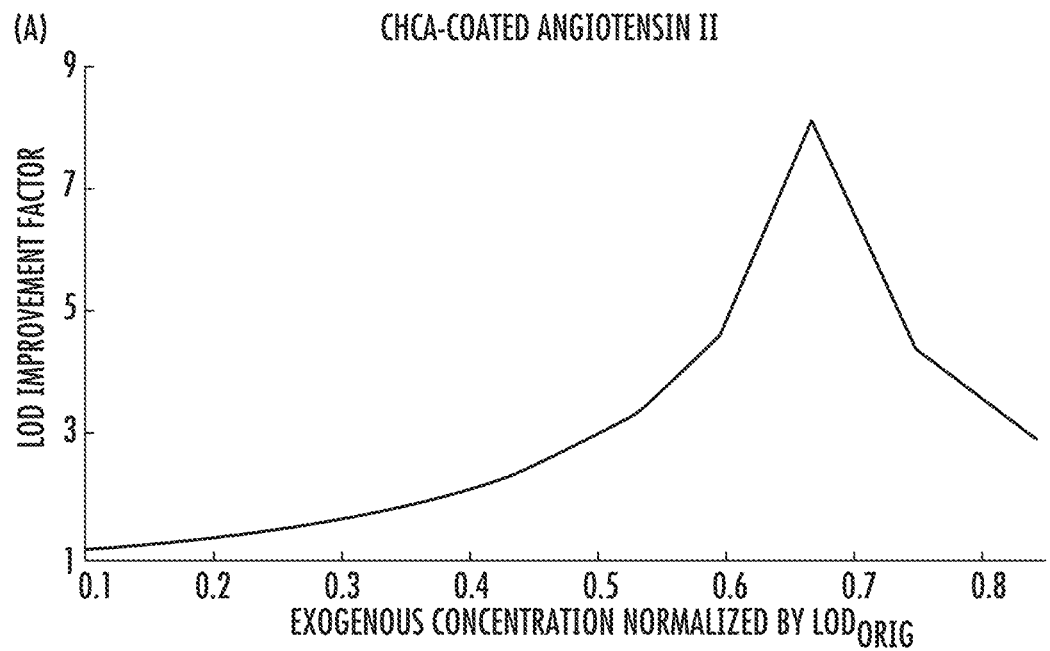
FIG. 16A-16B depicts an example of the predicted improvement factor for Angiotensin II in the simple background experiment using A) CHCA and B) DHB is shown. The highest improvement factor is achieved at exogenous concentrations close to the $LOD_{orig}$ of the target peptide for both CHCA (0.67 $LOD_{orig}$) and DHB (1.46 $LOD_{orig}$) matrices. Due to the increase in the standard deviation of the measurements, the improvement factor decreases at higher exogenous concentrations.
Figure 16B:
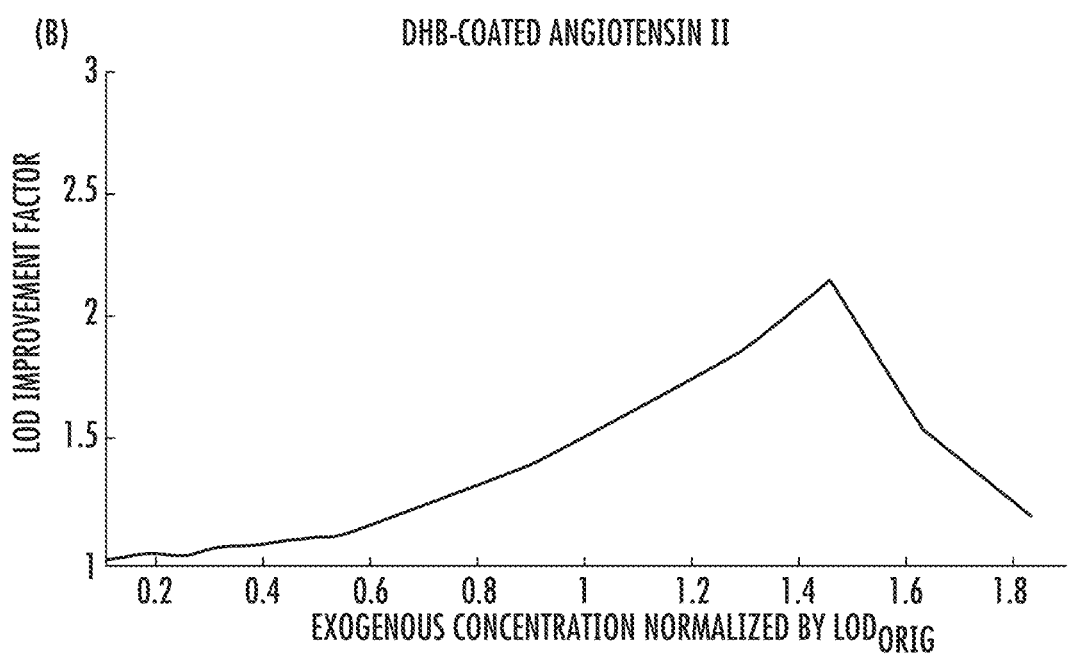

Additionally, we estimated the LOD improvement expected at each exogenous concentration using the MALDI-MS calibration curve for each peptide. The experimental $LOD_{orig}$ was calculated using eq1 and the predicted $LOD_C$ was estimated using eq 2 where the $LOD_{orig}$ and $LOD_C$ are graphically depicted in FIG. 11. For all three peptides, the predicted improvement factor is very close to 1 at the lower end of the target analyte spiking concentrations, but it has local maxima at the midranges and decreased at higher spiking concentration. For example, the predicted $LOD_C$ for Angiotensin II using CHCA and DHB matrices in the simple background experiment is plotted as a function of spiking concentration C divided by $LOD_{orig}$ (FIG. 16). Maximum predicted LOD improvement was achieved when the spiking peptide concentration is close to $LOD_{orig}$. For all three peptides, there is a local maximum on the estimated LOD curve (corresponding to an optimal LOD improvement) at a spiking concentration of the target analyte around the control $LOD_{orig}$. The optimal spiking concentration and the corresponding estimated LOD improvement factor for the three peptides are listed in Table 1. This quantitative method suggests that maximum improvement of the detection limit for low abundance analytes depends not only on the analyte but also on the MALDI matrix, which affect the signal to noise ratio of each analyte. Maximal improvement factor for the analyte of interest can be reached by spiking the target analyte at a concentration close to $LOD_{orig}$ into the unknown sample for the analysis of target analytes.

TABLE 1

The optimal exogenous concentrations and improvement factors
for simple background experiment averaged over four replicates.
The optimal exogenous concentration is close to $LOD_{orig}$. On average,
the optimal exogenous concentration is 1.26 $LOD_{orig}$ over all three
peptides in CHCA matrix, which is lower than the optimal exogenous
concentration of 1.58 $LOD_{orig}$ for DHB matrix. Additionally,
CHCA yields a higher predicted optimal improvement factor
compared to DHB matrix.

| Peptide | Matrix | Local maximum exogenous concentrations (C/$LOD_{orig}$) | Local maximum improvement factors ($LOD_{orig}$/$LOD_C$) |
|---|---|---|---|
| Angiotensin I | CHCA | 0.72 ± 0.09 | 3.80 ± 0.68 |
|  | DHB | 1.75 ± 0.62 | 2.58 ± 0.92 |
| Angiotensin II | CHCA | 0.85 ± 0.21 | 3.93 ± 1.41 |
|  | DHB | 1.83 ± 0.18 | 1.63 ± 0.22 |
| β-Amyloid (1-15) | CHCA | 2.21 ± 0.82 | 1.82 ± 0.31 |
|  | DHB | 1.17 ± 0.30 | 4.04 ± 1.28 |
| All three peptides | CHCA | 1.26 ± 0.47 | 3.18 ± 0.68 |
|  | DHB | 1.58 ± 0.21 | 2.75 ± 0.70 |

Example 4

Figure 17:
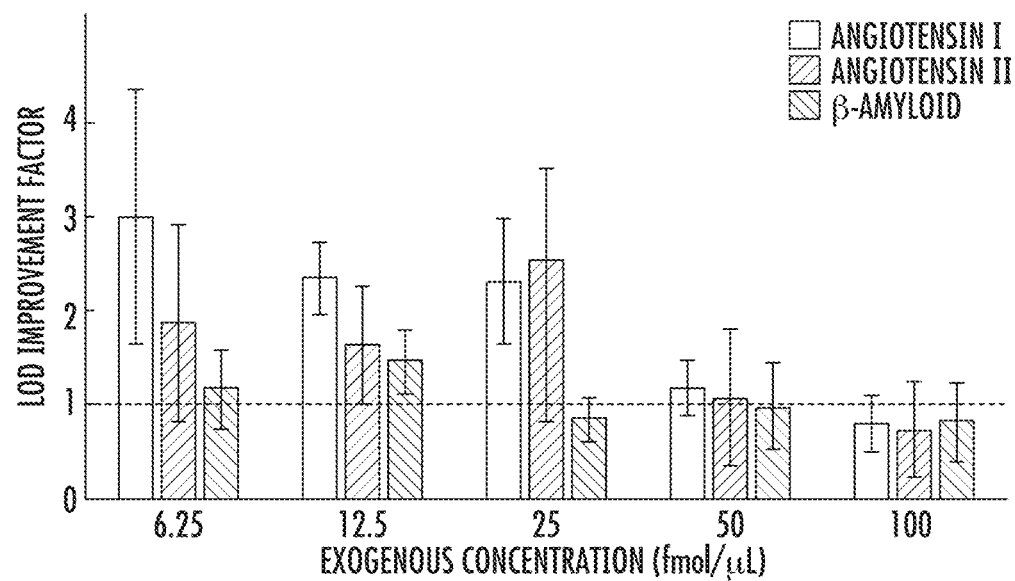
FIG. 17 shows experimental LOD improvement factors for three peptides in complex background using CHCA as the matrix are averaged over triplicate experiments. In 10 out of the 15 experiments, the LOD is improved. The improvement factors depend on the concentration of the exogenous analyte spiked into the sample as well as the analyte of interest. The error-bars depict the standard error of the mean.
Figure 18:
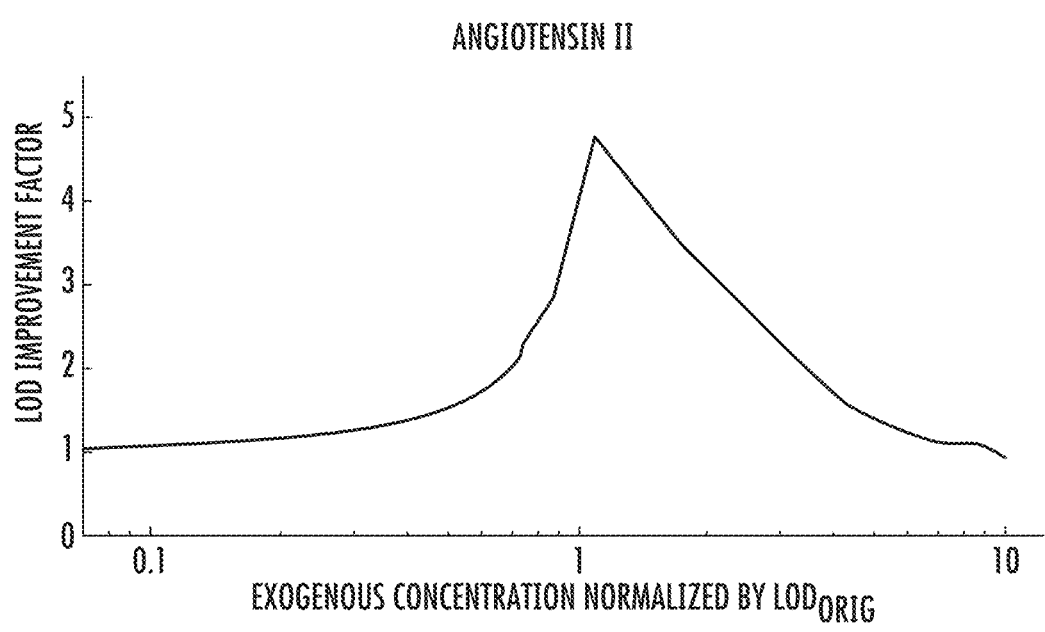
FIG. 18 depicts an example of predicted improvement factor for Angiotensin II in the complex background experiment. The highest theoretical improvement factor is achieved at exogenous concentrations close to the $LOD_{orig}$ of that peptide, similar to the simple background experiment. The curve is bell-shaped yielding an improvement factor close to 1 at lower concentrations, and decreasing at higher concentrations.

Determining LODs of Target Analytes in Complex Mixture. To determine whether the LOD improvement observed with a solution of a single analyte using the TAD method could apply to target analytes in a complex mixture, the above three target analytes were analyzed in the mixture of serum peptides. Five spiking concentrations of each target peptide were considered and the triplicate experiments were performed for each case. Of the fifteen experimental conditions (five exogenous concentrations for each of the three target peptides), the average LOD of triplicate experiments was improved in ten targeted peptide-exogenous peptide pairs compared to the corresponding control (FIG. 17). In general, highest spiking concentrations of target peptides result in low improvement factors, and in some cases fail to achieve any improvements. The estimated LOD curve for Angiotensin II in complex mixture shows similar pattern to the simple background experiment (FIG. 18), with a local maximum at exogenous concentration of $LOD_{orig}$. The optimal exogenous concentrations and the achieved improvement factors for complex background experiment are shown in Table 2. The optimal predicted exogenous concentrations are estimated to be close to 2 $LOD_{orig}$, which is slightly higher than that of the simple background experiment. Also, the predicted maximum LOD improvement factor in the complex background experiment is lower than that of the simple background experiment for the same three examined peptides.

TABLE 2

The optimal exogenous concentrations and improvement factors for complex background experiment using CHCA matrix averaged over triplicate independent experiments. On average, the optimal exogenous concentration required for predicted maximum LOD improvement factor is close to 2 $LOD_{orig}$.

| Peptide | Local maximum exogenous concentrations ($C/LOD_{orig}$) | Local maximum improvement factors ($LOD_{orig}/LOD_C$) |
| --- | --- | --- |
| Angiotensin I | 2.57 ± 0.31 | 3.05 ± 0.81 |
| Angiotensin II | 0.71 ± 0.31 | 1.85 ± 0.85 |
| β-Amyloid (1-15) | 3.15 ± 2.59 | 1.59 ± 0.48 |
| All three peptides | 2.14 ± 0.74 | 2.16 ± 0.45 |

TAD takes advantage of the carrier effect of standard additions to reveal the signal that is buried in noise due to complexity of the sample. The carrier effect is a repeatedly reported phenomenon, which to the best of our knowledge has not previously been used in quantitative mass spectrometry as a technique for improving the detection. TAD provides a 3-fold LOD improvement in simple background, and a 2-fold LOD improvement in complex background experiments. This enhancement achieved through TAD might be modest compared to signal enrichment techniques such as chromatography, fractionation, or affinity enrichment; however, TAD can be applied in combination with these techniques to further improve the detection limit by 2- to 3-fold. Also, further improvement of detection limit using TAD technique can be achieved by highly controlled conditions with high reproducibility. Therefore, the functionality of TAD might improve in a more controlled and reproducible experimental setting such as automated clinical assays and in targeted detection of glycans and proteins in situ by mass spectrometry as disclosed herein.

The presently disclosed methods include direct profiling of glycans on tissues, in situ chemical labeling and/or enzymatic modifications of glycans and glycoproteins on tissue slides, quantitative analysis of tissue glycans and glycoproteins using isotopic labeling, and targeted detection of glycans and proteins in situ by mass spectrometry.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method for direct mass spectrometry imaging of sialic acid residues in a sample where spatial distribution of the sialic acid residues in the sample is maintained, the method comprising:
   (a) obtaining a biological sample comprising a tissue section having at least one sialic acid on a solid support;
   (b) adding p-toluidine to the sample of (a);
   (c) denaturing the at least one sialic acid containing glycoprotein in the biological sample of (b);
   (d) applying at least one releasing agent onto the biological sample of (b) to release the at least one sialic acid containing glycan from the at least one sialic acid containing glycoprotein in the biological sample of (b);
   (e) performing raster analysis of the biological sample of (d) with a mass spectrometer laser in an X and Y direction and acquiring the mass spectra for each pixel generated from the analysis on the tissue and identifying the at least one sialic acid containing glycan at each pixel.

2. The method of claim 1, wherein the biological sample comprises a paraffin-embedded tissue.

3. The method of claim 1, wherein the biological sample comprises a formalin-fixed tissue.

4. The method of claim 3, wherein the biological sample is rehydrated prior to step (b).

5. The method of claim 1, wherein denaturing the at least one sialic acid containing glycoprotein comprises heating the biological sample and/or incubating the biological sample with a proteolytic enzyme for a sufficient period of time.

6. The method of claim 1, wherein releasing the at least one glycan occurs by using an enzyme selected from the group consisting of Endoglycosidase H (Endo H), Endoglycosidase F (EndoF), and N-Glycanase F (PNGaseF).

7. The method of claim 6, wherein releasing the at least one glycan occurs by using the enzyme PNGaseF.

8. The method of claim 1, further comprising after step (d) coating the biological sample with a matrix.

9. The method of claim 8, wherein the matrix comprises 2,5-dihydroxybenzoic acid (DHB).

10. The method of claim 1, wherein the mass spectrometry is MALDI-mass spectrometry.

11. The method of claim 10, wherein the MALDI-mass spectrometry comprises MALDI time-of-flight (TOF) mass spectrometry.

12. The method of claim 10, wherein the MALDI-mass spectrometry comprises MALDI-quadrupole ion trap (QIT)-TOF mass spectrometry.

\* \* \* \* \*